(12) United States Patent
O'Donnell

(10) Patent No.: US 9,173,729 B2
(45) Date of Patent: Nov. 3, 2015

(54) SURGICAL INSTRUMENT FOR TREATING FEMALE URINARY STRESS INCONTINENCE

(76) Inventor: Pat D. O'Donnell, Little Rock, AR (US)

( * ) Notice: Subject to any disclaimer, the term of this patent is extended or adjusted under 35 U.S.C. 154(b) by 1026 days.

(21) Appl. No.: 12/761,087

(22) Filed: Apr. 15, 2010

(65) Prior Publication Data
US 2010/0198001 A1 Aug. 5, 2010

Related U.S. Application Data

(60) Division of application No. 10/701,253, filed on Nov. 4, 2003, now Pat. No. 7,771,345, which is a continuation-in-part of application No. 10/308,735, filed on Dec. 3, 2002, now Pat. No. 6,808,486.

(51) Int. Cl.
*A61F 2/02* (2006.01)
*A61F 2/00* (2006.01)

(52) U.S. Cl.
CPC .................................. *A61F 2/0045* (2013.01)

(58) Field of Classification Search
CPC ....... A61F 2/02; A61F 2/0045; A61F 2/0063; A61F 2002/0072; A61F 2220/0016; A61F 2250/0007; A61F 2210/0004; A61F 2/0036; A61B 2017/00805; A61B 17/06109; A61B 17/0401; A61B 2017/0409; A61B 17/3468
USPC .......... 600/29, 30, 32; 128/885, 899; 606/151
See application file for complete search history.

(56) References Cited

U.S. PATENT DOCUMENTS

| | | | |
|---|---|---|---|
| 4,052,988 A | 10/1977 | Doddi et al. | |
| 4,441,496 A | 4/1984 | Shalaby et al. | |
| 4,564,013 A | 1/1986 | Lilenfeld et al. | |
| 5,112,344 A | 5/1992 | Petros | |
| 5,578,046 A | 11/1996 | Liu et al. | |
| 5,626,611 A | 5/1997 | Liu et al. | |
| 5,686,090 A | 11/1997 | Schilder et al. | |
| 5,899,909 A | 5/1999 | Claren et al. | |
| 6,031,148 A | 2/2000 | Hayes et al. | |
| 6,042,534 A | 3/2000 | Gellman et al. | |
| 6,093,200 A | 7/2000 | Liu et al. | |
| 6,273,852 B1 | 8/2001 | Lehe et al. | |
| 6,315,788 B1 | 11/2001 | Roby | |
| 6,319,264 B1 * | 11/2001 | Tormala et al. | 606/151 |
| 6,406,423 B1 | 6/2002 | Scetbon | |
| 6,502,578 B2 | 1/2003 | Raz et al. | |

(Continued)

OTHER PUBLICATIONS

Merriam Webster's Dictionary www.mirriam-webster.com /dictionary/progressive copywrite 2015 (viewed Apr. 15, 2015).*

(Continued)

*Primary Examiner* — Christine H Matthews
(74) *Attorney, Agent, or Firm* — Winstead, P.C.

(57) ABSTRACT

A suburethral sling device and method for treating female urinary stress incontinence which is anatomically configured to implant into the lower abdomen of a female in a manner providing support to mid-urethral and bladder neck sphincteric continence sites with the sling defining in part, mesh and tissue remodeling portions. The sling is deployed via a sling transfer instrument having distal and proximal ends with the instrument comprising in part a progressively curved shaft portion positioned between the distal and proximal ends. An insertion handle of the transfer instrument is secured to the curved metal shaft section guiding the shaft tip through the tissues of the abdomen in an anterior/posterior direction as well as a cephalad/caudad direction.

21 Claims, 11 Drawing Sheets

(56) References Cited

U.S. PATENT DOCUMENTS

| | | | |
|---|---|---|---|
| 6,592,515 B2 | 7/2003 | Thierfelder et al. | |
| 6,599,318 B1 | 7/2003 | Gabbay | |
| 6,607,525 B2 | 8/2003 | Franco | |
| 6,612,977 B2 | 9/2003 | Staskin et al. | |
| 6,800,082 B2 * | 10/2004 | Rousseau | 606/151 |
| 6,808,486 B1 | 10/2004 | O'Donnell | |
| 2002/0103542 A1 | 8/2002 | Bilbo | |
| 2002/0107430 A1 | 8/2002 | Neisz et al. | |
| 2003/0045774 A1 | 3/2003 | Staskin et al. | |
| 2003/0065246 A1 | 4/2003 | Inman et al. | |
| 2003/0171644 A1 | 9/2003 | Anderson et al. | |

OTHER PUBLICATIONS

Office Action from U.S. Appl. No. 12/761,167 dated Nov. 12, 2010.
Office Action from U.S. Appl. No. 12/761,167 dated Apr. 27, 2011.

* cited by examiner

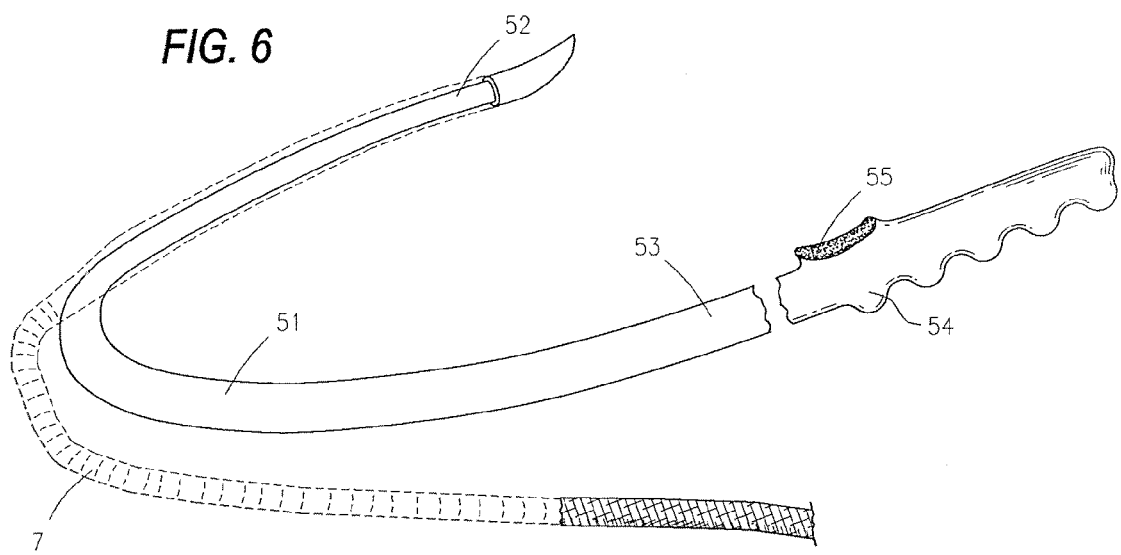

SURGICAL INSTRUMENT FOR TREATING FEMALE URINARY STRESS INCONTINENCE

CROSS-REFERENCE TO PENDING APPLICATIONS

The present application is a divisional application of co-pending U.S. patent application Ser. No. 10/701,253, entitled "A Surgical Instrument for Treating Female Urinary Stress Incontinence," filed Nov. 4, 2003, which is incorporated by reference herein. The present application claims priority benefits to U.S. patent application Ser. No. 10/701,253 under 35 U.S.C. §121. U.S. patent application Ser. No. 10/701,253 is a continuation-in-part application of U.S. patent application Ser. No. 10/308,735, which issued on Oct. 26, 2004 as U.S. Pat. No. 6,808,486, entitled "Surgical Instrument For Treating Female Urinary Stress Incontinence."

TECHNICAL FIELD OF THE INVENTION

The present invention relates to surgical instruments for treating female urinary stress incontinence problems generally and in particular, a suburethral, anatomically configured mesh sling for implanting into the lower abdomen of a female which provides simultaneous support to mid-urethral and bladder neck sphincteric continence sites.

BACKGROUND OF THE INVENTION

The suburethral sling technique for treatment of stress urinary incontinence has become the preferred treatment because the long term results are better in most cases than other treatment methods. The classic pubovaginal sling technique utilizes rectus fascia from the patient as the sling material for support of the urethra. The morbidity of rectus fascia pubovaginal sling procedures has caused surgeons to utilize alternative materials. Permanent non-absorbable materials have been deployed in one such alternative but have resulted in erosions of the synthetic material into the urethra and vagina. Also, infections of the sling have had serious complications because of the material being treated as a "foreign body".

Cadaveric tissue has been used in an effort to avoid the problem of "foreign body" reactions resulting in infections and erosions. However, cadaveric fascia and cadaveric dermis have not had the same results as tissue derived from the patient at the time of surgery. Cadaveric fascia is a tissue remodeling material. That is, the human body recognizes the tissue as a familiar material and biochemically breaks down the tissue and rebuilds it as its own tissue. Unfortunately, during the breaking down period of the cadaveric tissue, the tissue strength often fails rendering support of the urethra inadequate. Consequently, the urethra "falls" back down and the sling fails. Remodeling tissue needs to have additional strength during the time of remodeling in order to avoid failure of the material due to material weakness. Once remodeling has occurred, the tissue is strong enough to provide a good result for a long time.

Biodegradable materials such as polylactate are available that are degraded by the body slowly over 18 months to 30 months. These materials can be made into a mesh to support the tissue remodeling materials through the period of remodeling. This leaves normal body tissue supporting the urethra that has resulted from the remodeling process. The biodegradable sling material such as polylactate is absorbed by the body and there is no "foreign body" to create erosions and infections.

Deployment of the current sling devices utilize complicated sling transfer instruments that cannot be well controlled by the surgeon. This has resulted in serious complications including perforation of bowel as well as injury to major arteries and veins causing death in young women who are otherwise healthy having a simple surgical procedure. It is critical that the sling transfer instrument be simplified and better control of the instrument be provided to the surgeon.

As the urethra prolapses or "falls down" resulting in loss of bladder control, the entire vaginal wall also prolapses or "falls down". Current sling procedures do not provide any support for the anterior vaginal wall. One of the most common causes of re-operation after current sling procedures is a cystocele repair to repair the anterior vaginal prolapse that should progressively worsened after the sling placement. Current slings are not designed to repair the anterior vaginal wall at the same time the support of the urethra is done. A sling is needed that supports the entire functional urethra as well as the base of the bladder to prevent progression of vaginal prolapse.

The normal woman when in the standing has the urethra in a position that the axis through the urethra is 15 degrees to 35 degrees off a true vertical position. The pubic bone has an axis of about 45 degrees off a true vertical position. This makes the angle or the axis of the pubis and the angle of the axis of the urethra about 70 degrees to 90 degrees. The base of the bladder as it attaches to the urethra has a posterior angle of 90 degrees to 115 degrees. The contoured sling is designed to restore the urethro-vesical angle and to restore the axis of the urethra.

Deployment of contemporary sling devices utilize complicated sling transfer instruments that cannot be well controlled by the surgeon. This has resulted in serious complications including perforation of bowel as well as injury to major arteries and veins causing death in young women who are otherwise healthy having a simple surgical procedure. In keeping with the teachings of the instant invention, it is critical that a sling transfer instrument be simplified to allow enhanced instrument control by the surgeon.

Given the deficiencies of the contemporary art and the enhancement teachings of the instant invention, it is an object of the instant invention to provide a tubular mesh sling for incontinence which eliminates urethral obstruction and voiding difficulties associated with slings and tapes of the contemporary art.

It is another object of the instant invention to provide an incontinence solution which avoids the morbidity associated with rectus fascia tissue transplanted from the abdomen to the vagina of a patient and the long term durability deficiencies of cadaveric tissue as used in the contemporary art.

It is a further object of the instant invention to provide an incontinence solution which avoids the numerous and serious complications from intra-operative injury to organs in the pelvis.

It is yet another object of the instant invention to avoid paravaginal dissection required of surgical instruments and methodologies associated with the contemporary art.

A further object of the instant invention is to provide an incontinence solution which is embodied as a sling design conforming to the anatomical variations of the urethra of women who have urinary incontinence.

A yet further object of the instant invention is to provide a knit mesh pubovaginal sling which conforms to the anatomy of the urethra and anterior vaginal wall when the anatomy of a patient is distorted by urethral prolapse or previous vaginal surgery.

Another object of the instant invention is to present a mesh sling embodiment in a component structure that has an anterior surface which attaches to the vaginal wall adjacent to the urethra and a posterior surface which attaches to the vaginal mucosa.

An additional object of the instant invention is to provide an incontinence solution in a mesh sling form which avoids buckling due to opposing forces of the vaginal wall and vaginal mucosa on the sling.

A further object of the instant invention is to provide a mesh sling which has an anterior and posterioral layer which provides greater tensile strength compared to tape mesh slings of the contemporary art.

Yet another object of the instant invention is to provide a mesh sling design which demonstrates a significant degree of elasticity of the sling material.

A further object of the instant invention is to provide a tubular mesh sling which embodies a dual continence design and can be positioned to support both the mid-urethra and bladder neck sphincteric continence sites.

Another object of the instant invention is to provide a sling comprised in part of tissue remodeling material where sufficient support is provided to tissue remodeling material during biochemical breakdown of the tissue and rebuilding.

Another object of the instant invention is to provide a sling which is comprised of biodegradable materials and tissue remodeling materials.

A further object of the present invention is to disclose and teach a sling transfer instrument which allows enhanced sling deployment control by a surgeon.

Another object of the instant invention is to teach a method and apparatus for sling deployment utilizing either suprapubic, transvaginal or obturator fossa deployment methodologies.

A further object of the instant invention is an anterior vaginal sling that restores anatomical support to both the mid-urethral continence sphincteric function and the bladder neck continence sphincteric function.

Another object of the instant invention is an anterior vaginal sling that restores the anatomical relationship of the urinary bladder to the urethral by providing confluent support to the base of the bladder and the proximal urethra.

A further object of the instant invention includes an anterior vaginal sling that is contoured to restore the normal anatomical position of the mid-urethra, the proximal urethra, the bladder neck, and the base of the bladder which not only restores the normal continence sphincteric function of the urethra but also restores normal bladder function relative to the urethra.

Yet another object of the invention provides an anterior vaginal sling composed of biodegradable mesh or non-biodegradable mesh in any non-proprietary weave configuration.

An object of the instant invention provides an anterior vaginal sling design using biodegradable mesh reinforced tissue remodeling material with the biodegradable mesh combined with tissue remodeling material to provide tensile strength for the tissue remodeling material during an interval of tissue weakness due to the process of remodeling. The biodegradable material can be layered, stranded, or randomly combined with tissue remodeling materials.

Still yet, another object of the instant invention provides a sling transfer instrument that has a progressively curved shaft portion and a sharply curved tip that allows the instrument to be passed through the retropubic space with a reduced risk of organ perforation.

Further, an object of the instant invention provides the sling has supporting ribs throughout the distal part of each end of the sling to secure the sling to surrounding tissues and to allow for sling tension adjustment.

Another object of the instant invention includes a biodegradable tab which is located at the middle of the sling and extends through the vaginal mucosa postoperatively to allow loosening of the sling tension postoperatively if necessary.

A further object of the instant invention provides that the distal segment of each end of the sling is left in place postoperatively to allow tightening of sling tension if necessary. An attachable handle is used postoperatively for sling tension adjustment.

Yet another object of the present invention provides a spring design sling tension adjustment instrument that is used intra operatively to insure proper sling tension.

A further object of the present invention provides an extended embodiment of the sling that is used to provide support to the proximal segment of the anterior vagina to support cystocele repair.

An additional object of the present invention provide that the sling transfer instruments are designed with a luminous coating for easy identification during cystoscopy should perforation of the bladder occur.

Another object of the present invention is to provide a sling transfer instrument with detachable insertion handle designed to provide maximum control to the surgeon of the instrument tip to avoid organ perforation. Finger grips and a specially designed thumb control feature of the handle provides accuracy of tip placement.

An alternative object of the present invention provides that the embodiment of the sling transfer instrument design is used for placement from a suprapubic position through the prevesical space into the vagina. The sling is attached to the tip of the instrument and transferred to the suprapubic position.

SUMMARY OF THE INVENTION

The pubovaginal sling of the instant invention is a tubular layered sling configuration. A mesh comprised of a biodegradable polymer such as polylactate is placed around a layer of tissue remodeling material such as cadaveric fascia to form a tubular layered sling configuration. The biodegradable polymer segment of the sling provides tensile strength to the tissue remodeling material throughout the remodeling period until the remodeled tissue has achieved maximum tensile strength. After the remodeled tissue has formed, the biodegradable polymer will begin to lose tensile strength and disappear through biodegradation, leaving normal body tissue from the remodeled material in position to support the anterior vaginal wall and urethra without "falling down" during tissue remodeling when the remodeling material is weakened by the remodeling process of the body. The layered sling configuration can be constructed with the tissue remodeling material layered between two layers of biodegradable material in a tubular configuration. The tubular sling may be configured from multiple layers of a single biodegradable material or it can be configured using multiple layers of different biodegradable materials. Multiple layers of a single tissue remodeling material may be used or multiple layers of different remodeling materials may be used.

An embodiment of the tubular layered sling configuration includes a central tubular configuration of biodegradable mesh surrounded by a tubular sling comprised of tissue remodeling material. An alternative embodiment includes a non-biodegradable tubular mesh sling that can be placed between layers of tissue remodeling materials. An alternative embodiment includes a tubular mesh sling that has a central segment that is non-biodegradable with a distal segment that is biodegradable. Finally, an essential embodiment of the tubular sling design includes tubular distal segments with a layered non-tubular central segment.

The layered tubular sling configuration of the instant invention has a unique design that is contoured to the anatomical configuration of the mid-urethra, the proximal urethra, and the base of the bladder. The contoured sling restores the normal anatomical relationship between the urethra and the bladder. Restoring the normal anatomical relationship of the urethra to the urinary bladder results not only in urinary continence but also enables normal voiding to occur following the operative procedure. Urinary continence is only part of the desired surgical outcome, however normal voiding following surgery is equally important as urinary continence for surgical management of incontinence in women.

Slings of the contemporary art are often represented as a "tape" sling and do not restore the normal anatomical relationship of the urinary bladder to the urethra. The contoured tubular sling is shaped to restore the normal anatomy of the urethra and the base of the bladder. The restoration of the normal anatomical position of the urethra relative to the urinary bladder is critical for normal voiding following incontinence surgery. One of the most common problems following incontinence surgery using tape slings is bladder obstruction due to an abnormal anatomical relationship between the bladder and the urethra. The contoured tubular sling avoids the anatomical obstruction from the current "tape" slings by providing support for the urethra and bladder with the normal anatomical contour. In the instant invention, the normal anatomical position is restored not only of the urethra but also the base of the bladder. The most critical objective that must be accomplished is restoration of the anatomical relationship between the urethra and the bladder in order for normal voiding to occur after surgery.

Voiding dysfunctions including urinary frequency, urinary urgency, and nocturia are common problems after current sling procedures because the normal anatomical relationship between the urethra and the bladder is not restored. The focus of treatment of stress urinary incontinence in women has been the urethra alone with methods to support the urethra to prevent incontinence with coughing or sneezing. The anatomical relationship of the urethra to the bladder has not been maintained with "tape slings" and the result has been postoperative voiding dysfunctions. The contoured tubular sling provides support to the functional urethral which is the mid-urethra, the proximal urethra and the bladder neck. In addition, the contoured tubular sling provides support to the base of the bladder which prevents voiding dysfunctions in women following surgery.

An alternative embodiment of the contoured tubular sling using the layered sling configuration design is "extended support" of the anterior vaginal wall to include the entire anterior vaginal wall. This "extended support" provides surgical management of cystocele repair in combination with incontinence surgery. The "extended support" design has eyelets for suture placement or tissue anchor placement to secure the vaginal support segment of the tubular sling in position. An alternative embodiment of the "extended support" design of the layered sling configuration includes segments of different size and shape that are required to support vaginal vault repair including cystocele repair, enterocele repair, and rectocele repair.

The distal segments of the layered tubular sling configuration is approximately 1 centimeter in width and has small "ribs" that pass transversely through the sling to secure the sling in position. The "rib" design eliminates the need for the plastic sheath of current slings. The plastic sheath of current slings is difficult to remove and excess sling tension is often a complication of intra operative sheath removal.

The sling tension is adjusted using a spring loaded sling tension adjustment device. The sling tension adjustment device is designed to avoid the problem of the sling being placed with too much tension around the urethra which results in urinary retention following surgery. During the surgical procedure, the sling is tightened until the spring is compressed and the sling tension device is closed which results in appropriate sling tension.

The "confluent" sling transfer instrument is a unique design that is passed from the vagina through the retropubic space. The tip of the transfer instrument has a reverse curve shape that keeps the tip in immediate contact with the pubic bone during placement of the instrument which avoids injury to the bladder, adjacent bowel or major arteries and veins. The preferred shape of the confluent sling transfer instrument is square with rounded corners. Alternative embodiments include oval shape and rectangular shape. The diameter of the curvature of the instrument is approximately 23.5 cm with a radius of approximately 8 cm. The proximal 6 cm of the instrument is straight and inserts into a handle. The handle is detachable which allows the sling transfer instrument to be passed from a transvaginal position to the suprapubic area on both the right and left side. A transfer handle is attached on the tip of the instrument in the suprapubic area and the insertion handle is detached to allow attachment of the sling. This allows the sling transfer instrument to be inserted transvaginally and passed through the retropubic space, the tip in the suprapubic area is then controlled by an attachable transfer handle, the insertion handle is detached, the sling is attached to the base of the instrument where the insertion handle was located, and the sling transfer instrument is pulled through the retropubic space in a single pass with a confluent motion. Once the sling is positioned in the suprapubic position, the sling is cut near the tip and the sling transfer instrument is removed on both the right and left side.

After the sling transfer instrument is passed through the retropubic space, cystoscopy is done to insure that the instrument did not inadvertently pass through the urinary bladder. Since it is difficult to see a gray colored metal transfer instrument on endoscopic examination of the bladder, the confluent sling transfer instrument is covered with a luminous material to allow it to be easily identified endoscopically. The "luminous" feature of the confluent sling transfer instrument reduces the risk of unrecognized bladder perforation by the sling transfer instrument because it can be seen more easily on endoscopic examination of the bladder. Such luminous materials include but are not limited to fluorescent dyes, paints and coatings.

The handle of the instrument is a critical feature of control of the instrument by the surgeon. The insertion handle is critical in determining the retropubic path of the instrument during passing of the instrument. The handle used is the same design described previously which allows the surgeon to precisely guide the tip of the sling transfer instrument against the pubic bone through the retropubic space during placement of the instrument which prevents injury to bowel, bladder, and major arteries. The size and shape of the handle allow the surgeon to have maximum control of the reverse curve tip of the instrument which is positioned against the pubic bone at all times during placement which avoids injuries from the instrument.

When the transvaginal approach to placement of the contoured design of the layered tubular sling configuration is done, the confluent sling transfer instrument is passed from the vagina through the retropubic space. The thumb control of the introducing handle is used to maintain the reverse curve tip of the confluent sling transfer instrument directly in contact with the pubic bone throughout the retropubic placement of the instrument. When the tip of the confluent transfer instrument exits the skin in the suprapubic area, the transfer handle is attached to the tip of the instrument and cystoscopy is performed to insure that the sling transfer instrument did not pass through the bladder. With the transfer handle on the tip of the confluent transfer instrument to stabilize the instrument in position, the thumb controlled introducing handle is disengaged from the proximal end of the instrument and removed. The sling attachment tip is placed on the proximal end of the instrument where the thumb control handle was located, and the transfer handle that has been placed on the distal tip of the instrument is used to pull the confluent sling transfer instrument through the retropubic space along with the sling attachment tip and the distal end of the sling. The sling tension adjustment spring device is placed between the sling and the anterior vaginal wall. When the spring is compressed, the sling adjustment device is removed. The excess sling length in the suprapubic area is cut at the skin level.

In women who have complicated incontinence such as failed previous surgery, the excess sling is cut 3 cm above the skin level. An antibiotic dressing is used to cover the ends of the sling. At approximately three days following surgery, the dressing is removed and sling tension is adjusted. Sling tension is increased by placing the sling adjustment handles on the excess sling material in the suprapubic area and applying increased tension to the sling along the anterior vaginal wall. When sling tension has been adjusted to the desired level, the excess sling material is removed. When sling tension is too tight, the sling adjustment tab in the vagina is grasp with an instrument and the sling tension is reduced by applying downward tension. The sling tension postoperatively is adjusted based on the clinical ability of the patient to void. When ideal sling tension is achieved, the sling adjustment tab in the vagina is cut at the vaginal mucosa level. Also, the ends of the sling in the suprapubic area are cut at the skin level.

It is to be understood that both the foregoing general description and the following detailed description are exemplary and explanatory only, and are not restrictive of the invention as claimed. The accompanying drawings, which are incorporated herein by reference, and which constitute a part of this specification, illustrate certain embodiments of the invention and, together with the detailed description, serve to explain the principles of the present invention.

Further, the purpose of the foregoing abstract is to enable the U.S. Patent and Trademark Office and the public generally, and especially the design engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

In this respect, before explaining at least one embodiment of the invention in detail, it is to be understood that the invention is not limited in this application to the details of construction and to the arrangement so the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore that the claims be regarded as including such equivalent constructions insofar as they do not depart from the spirit and scope of the present invention.

DESCRIPTION OF THE DRAWINGS

FIG. 6 is an illustration of sling transfer tool as used in obturator fossa deployment embodiments.

DESCRIPTION OF THE PREFERRED EMBODIMENT

While the making and using of various embodiments of the present invention are discussed in detail below, it should be appreciated that the present invention provides for inventive concepts capable of being embodied in a variety of specific contexts. The specific embodiments discussed herein are merely illustrative of specific manners in which to make and use the invention and are not to be interpreted as limiting the scope of the instant invention.

Figure 1:
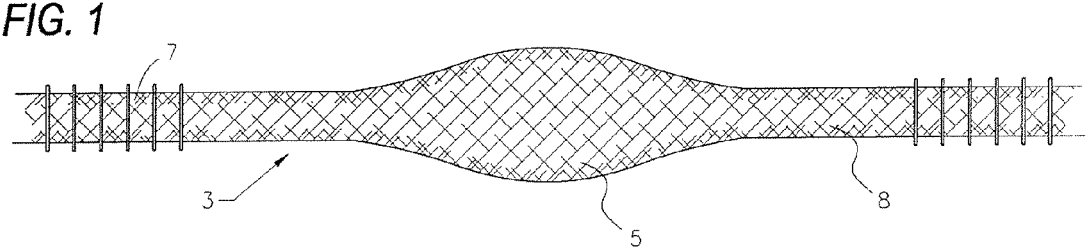
FIGS. 1 through 1B illustrate the mesh sling of the instant invention distinguishing further its tubular mesh and tissue remodeling material components.
Figure 1B:
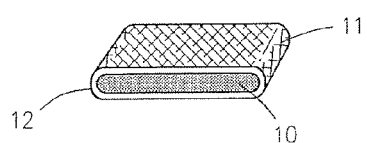

FIGS. 1 through 1B illustrate the mesh sling of the instant invention distinguishing further its tubular mesh and tissue remodeling material components. Turning now to FIG. 1 through 1B. In FIG. 1 it may be observed where the mesh sling is generally referred to as element 3 and is comprised of a generally central segment 5 and distal segments 7 and 8. The central segment 5 of the tubular mesh sling 3 is approximately 2.5 cm wide and 4.0 cm long with a rapid taper over approximately 1.5 cm down to a size of 1.0 cm in width at distal ends 7 and 8. Each distal section 7 and 8 may be covered with a circular plastic sheath which extends and overlaps in the central segment 5. The plastic sheath(s) are removed at the end of the sling's deployment procedure. Though variable and appropriate dimensions may be had with respect to the sling of the instant invention, the sling's deployment is most effective when practiced at an approximate length of 60 cm and 4.0 cm central section to position and support the bladder neck sphincteric and mid-urethral sphincteric sites as well as support for the base of the bladder.

FIG. 1B is a cross-sectional view of the sling of FIG. 1 illustrating relative positioning of tissue remodeling material 10, the sling's center most portion and mesh portions 11 and 12 substantially surrounding/sandwiching to tissue remodeling portion 10. Said tissue remodeling portion 10 and mesh portions 11 and 12 are bonded or otherwise fixedly attached to one another by surgical adhesive means or suturing means well known to skilled practitioners of the art.

Figure 1C:
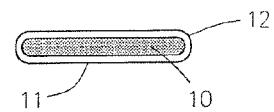

FIG. 1C illustrates a partial sectionalize view of the distal segments 7 or 8 wherein tubular mesh sections are again defined as elements 11 and 12 and substantially surround tissue remodeling material 10. Various tissue remodeling materials may be used with respect to practicing the sling of the instant invention including homologous tissues and heterologous tissues. The mesh portions of the sling of the instant invention 11 and 12 are non-limitedly comprised of non-absorbable polymers, such as polypropylene, and possess a filament size of approximately 0.006 of an inch. Biodegradable mesh portions are non-limitedly, absorbable polymers, such as polylactate with a filament size of approximately 0.015 of an inch. To those skilled in the art it will become readily apparent that for rapidly absorbable biopolymers a larger filament size can and should be practiced. As disclosed in the parent application, a combination of filament patterns may be used to represent the knit pattern such as but not limited to a simple knit, a complex knit, or woven pattern. The knit pattern may have seams or be seamless and with the size of the filaments dependent upon the clinical application may be simple knit, complex knit, or woven pattern and such knit patterns may have seams or be seamless. The size of the filament is dependent upon the clinical application and chemical composition of the knit. The center segment may be a non-absorbable material with absorbable distal segments which provides a permanent support around the urethra and bladder neck while the retro pubic segment is absorbable and disappears over time.

Figure 2:
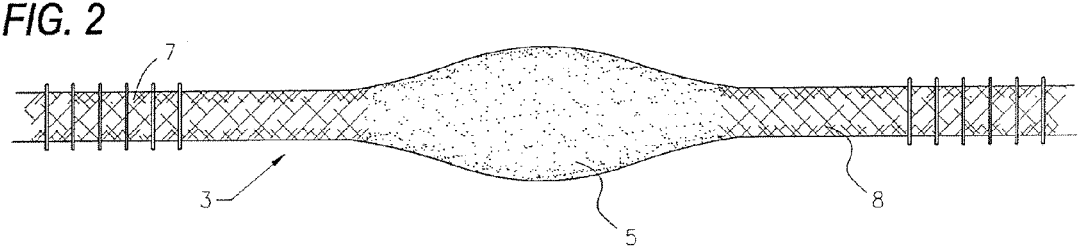
FIGS. 2 through 2A illustrate the mesh sling of the instant invention wherein tubular mesh and tissue remodeling materials have been structured and presented in an alternative structural relationship than that disclosed in FIGS. 1 through 1B.
Figure 2A:
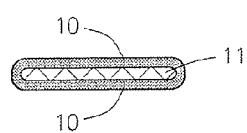

FIGS. 2 through 2A illustrate a readily envisioned alternative embodiment of the instant invention wherein the center most section 5 has been replaced with an alternative positioning structure of mesh materials 11 and 12 and tissue remodeling material 10. Stated succinctly, the mesh sling of FIGS. 2 and 2A comprises a center most position wherein tissue remodeling material 10 substantially surrounds and sandwiches mesh section 11. Further clarification with respect to the non-limiting alternative embodiment illustrated in FIG. 2 will be presented in conjunction with discussion of FIG. 3A.

Figure 3:
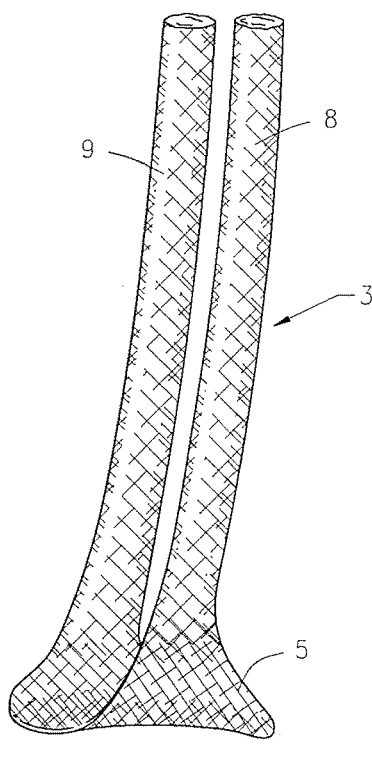
FIG. 3 is an illustration of the tubular sling of the instant invention providing further details with respect to its anatomical contoured design.

FIG. 3 is an illustration of the tubular sling of the instant invention providing further details with respect to its anatomical contoured design. Turning now to FIG. 3.

In FIG. 3 it is seen where the tubular mesh distal sections 8 and 9 attach in a graduating manner to contoured sling center most section 5 wherein center most section 5 as disclosed in FIG. 3 is contoured to support both mid-urethral and bladder neck sphincteric continence sites as will be discussed further in association with FIG. 4. FIG. 3 illustrates further the positional structuring of tubular mesh and tissue remodeling materials as discussed in association with FIGS. 1 through 1B. The normal anatomical relationship between the bladder and urethra is restored by additional support to the base of the bladder.

Figure 3A:
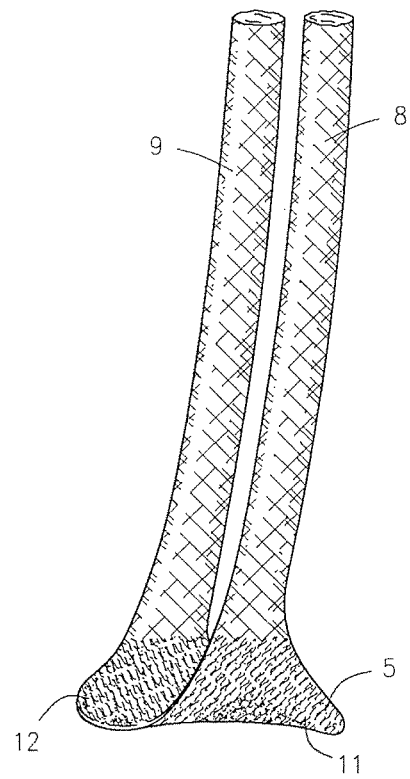
FIG. 3A is an illustration of the sling of FIG. 3 providing further detail with respect to the center most position of the tubular sling and its tissue remodeling material component.

FIG. 3A provides greater specificity and illustrates the positional structures of mesh and tissue remodeling material as presented in associated with discussion of FIGS. 2 and 2A wherein distal ends 8 and 9 are shown presenting a tubular mesh sector (innermost presentation not disclosed in FIG. 3A) and where the center most section of the contoured sling 5 is illustrated as comprising tissue remodeling material 11 to sandwich or otherwise encase tubular mesh section at contoured sling section's 5 center most portion. The mesh of the center portion 5 may be composed of the same material as the distal segment 8, 9 or the mesh material 5 may be different from 8, 9 including, but not limited to, biodegradable material combined with non-biodegradable material.

Figure 4:
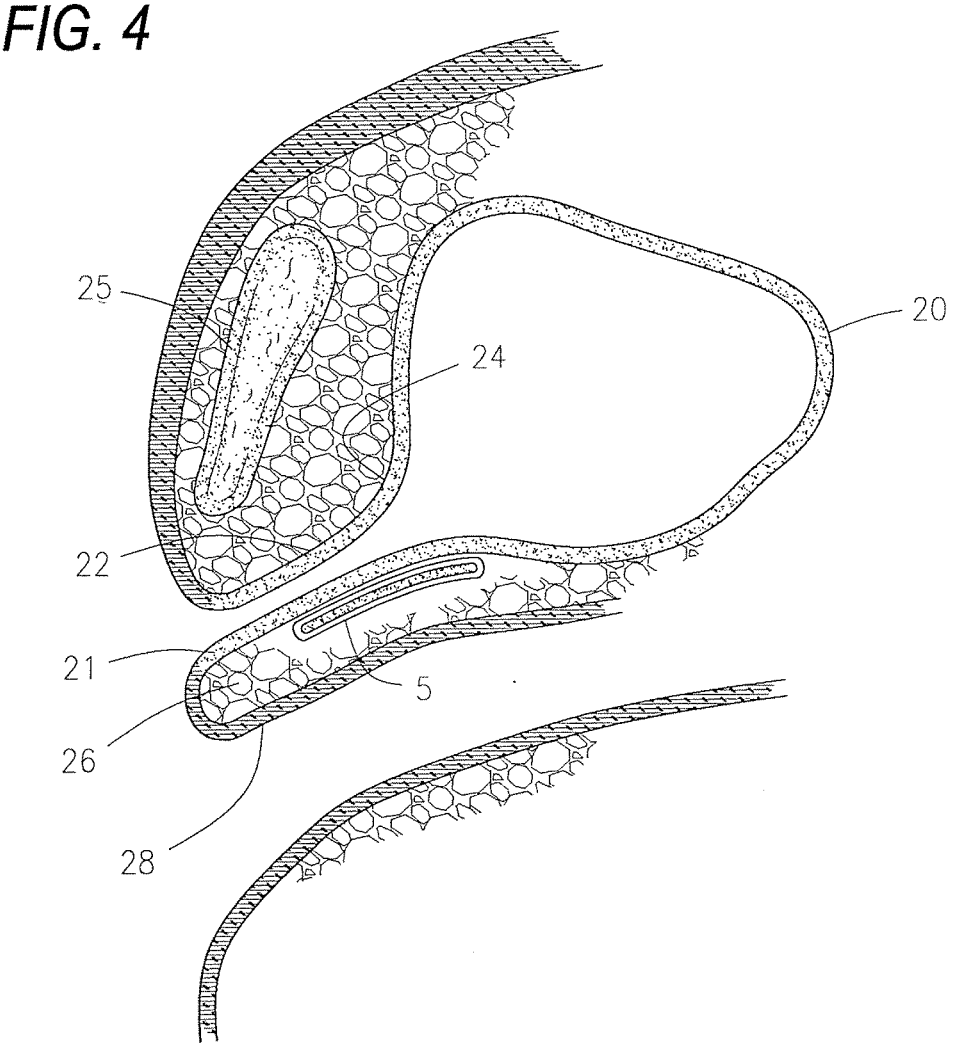
FIG. 4 is an illustration of the tubular sling of the instant invention as positioned to anatomically support mid-urethra and bladder neck sphincteric continence sites as well as the base of the bladder.

FIG. 4 is an illustration of the tubular sling of the instant invention as positioned to anatomically support mid-urethra and bladder neck sphincteric continence sites as well as the base of the bladder to restore the normal anatomical relationship of the bladder to the urethra. Turning now to FIG. 4.

In FIG. 4 it is observed where the contoured sling of the instant invention 5 is shown properly positioned to support bladder 20 and urethra 21 sphincteric continence sites respectively labeled 22 the mid-urethral continence site and 24 the bladder neck continence site. For purposes of full and enabling disclosure and ease of reference, FIG. 4 further provides detail with respect to the positioning of pubic bone 25, vaginal wall 26 and vaginal mucosa 28.

Figure 5:
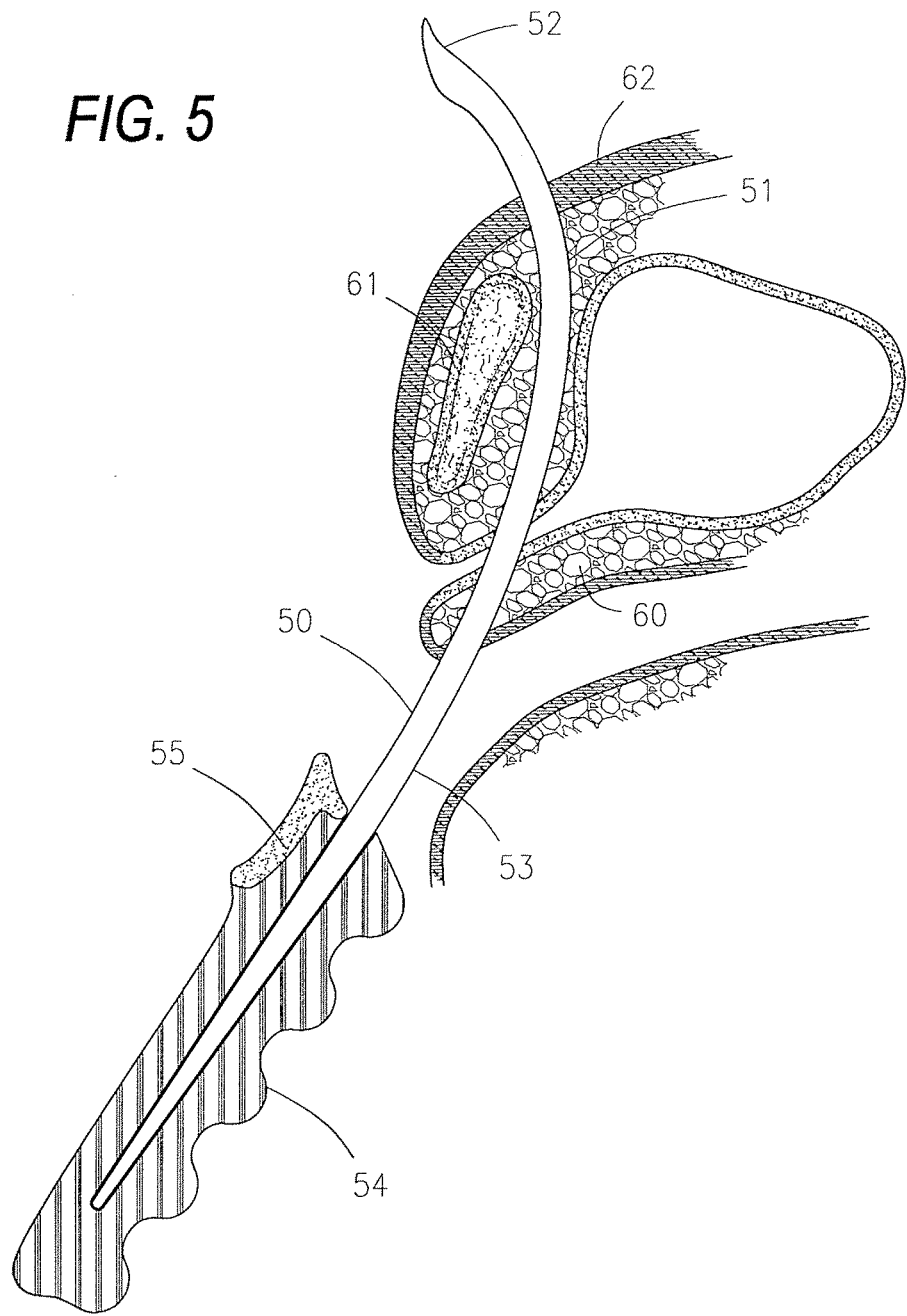
FIGS. 5 through 5B are illustrations of the sling transfer instrument tool as used in transvaginal and suprapubic deployment methodologies.
Figure 5A:
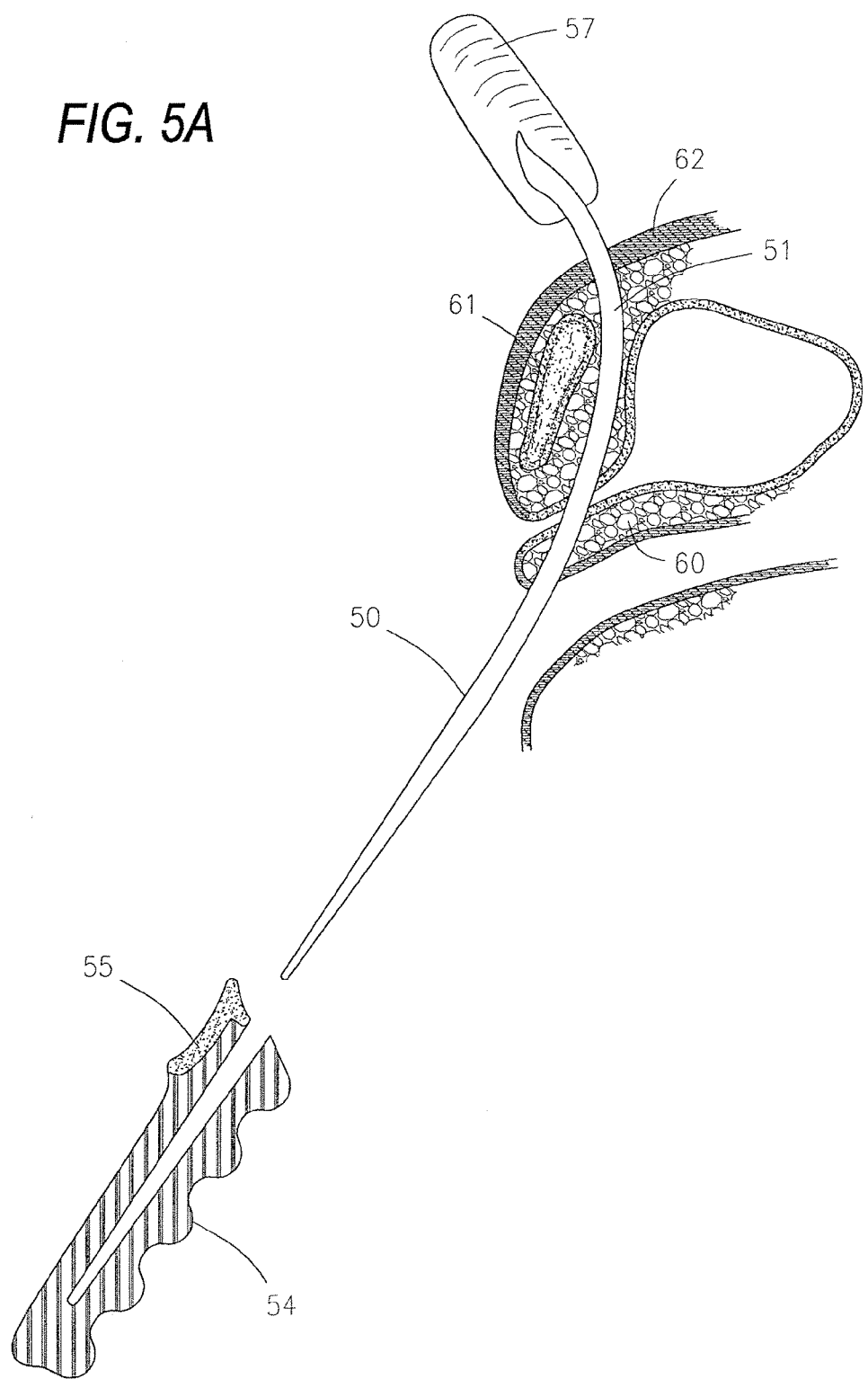
Figure 5B:
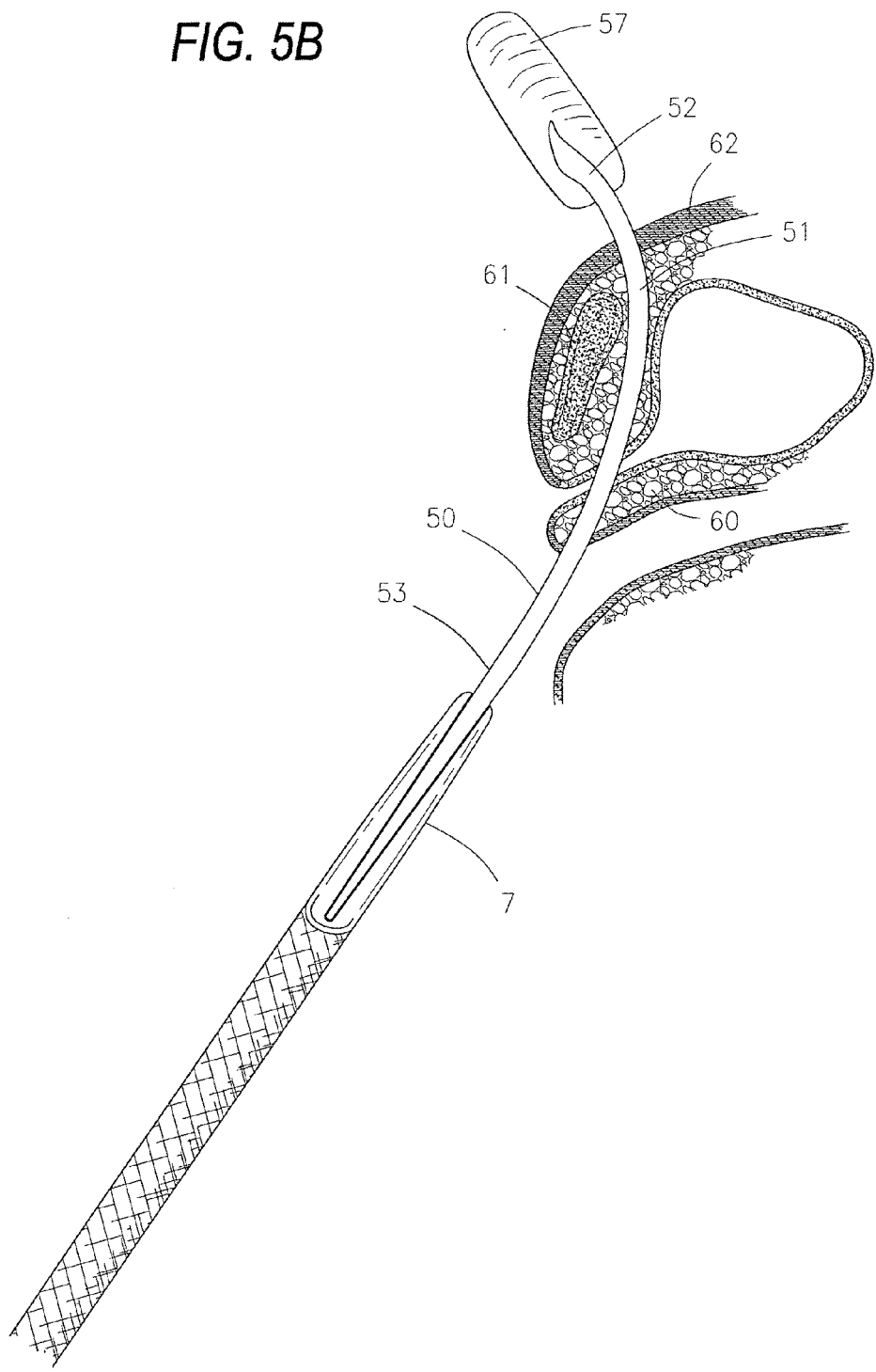

FIGS. 5 through 5B will further illustrate and disclose the sling transfer instrument of the instant invention as well as its deployment methodologies with respect to transvaginal utilization. Turning now to FIGS. 5 through 5A. In FIGS. 5 through 5A it is seen where the sling transfer instrument defines in part a progressively curved shaft portion 51 positioned between distal 52 and proximal ends 53. An attached handle 54 located at the shaft's proximal end 53. The sling transfer instrument 50, attached handle 54 further comprises a digit control accommodation 55 with said digit control accommodation dimensioned approximately 2.5 to 4.5 cm in length, 1.0 to 4.0 cm in width and approximately 1.5 cm in depth. The progressively curved shaft portion 51 of the sling transfer instrument has a diameter of about 3.5 mm to about 4.0 mm and a progressive curve with a maximum radius of approximately 5.1 cm. As can be seen in FIG. 5, the distal end 52 of shaft portion 51 is oriented in a direction opposite that of said shaft's curved portion. The distal end of the shaft portion oriented in a direction opposite of the shaft's curved portion is referred to as shaft tip portion and is approximately 1.0 cm in length and approximately 4.0 mm in width at an end opposite the end with handle 54 attached to shaft end portion 53.

FIG. 5B further illustrates a distal end of sling 7 which illustrates a mesh portion comprised of non-absorbable polymers and filaments having a diameter from 0.002 inch to about 0.08 inch. Alternatively, the mesh sling distal portion 7 may be comprised of absorbable polymers and filaments with said filaments forming a mesh pattern having a diameter from about 0.12 inch to about 0.1 inch. As discussed in association with FIGS. 1 and 2, the mesh sling is approximately 1.0 cm wide at proximal and distal ends (proximal end not illustrated in FIG. 5B) and a center most portion approximately 2.5 cm in length and 1.5 cm to 3.0 cm at its widest and generally center most position.

As an alternative to transvaginal and suprapubic deployment, an obturator fossa sling transfer instrument may be used for this particular type of deployment methodology. An example of the exaggerated curvature distinguishing sling transfer instruments used in association with transvaginal deployment (as illustrated in FIGS. 5 through 5B), FIG. 6 illustrates the progressively curved portion of the obturator fossa deployment embodiment wherein the progressively curved shaft portion 51 has a diameter from about 3.0 mm to about 4.5 mm and a progressive curve with a maximum radius of approximately 5.0 cm. Distal portions of said shaft 52 and handle portion (not illustrated in FIG. 6) remain consistent with specifications disclosed in association with FIGS. 6, 6A, 10 and 11 of the parent application (Ser. No. 10/308,735).

Returning now to FIGS. 5 through 5B wherein the invention's deployment methodology for transvaginal practice is disclosed. With respect to transvaginal deployment, a sling of the type disclosed in detail in association with either FIG. 1 or 2 is provided with the sling defining in part a tissue remodeling portion and a mesh section and contoured to the anatomical configuration of the mid-urethra, proximal urethra and base of the bladder. A sling transfer instrument 50 is next provided having a distal end 52 and a proximal end 53 with a progressively curved shaft portion 51 positioned between said distal 52 and proximal 53 ends with a detachable insertion handle 54 located at the instrument 50 proximal end 53. The sling transfer instrument is positioned with the detachable insertion handle 54 grasped within the human hand and using the handle 54, the instrument guides the distal tip portion 52 through the vaginal wall 60 behind the pubic bone 61, through the abdominal wall 62 and exiting the abdominal wall 62 below the pubic hair line. The detachable insertion handle 54 is next disengaged from the proximal end 53 of the sling transfer tool 50 after the sling transfer handle 57 is attached to the sling shaft curved tip 52. The distal end of sling 7 is next attached to the sling transfer's proximal end 53. The handle so attached 57 is then positioned within the human hand and using said handle 57, the sling transfer shaft is retrieved or otherwise pulled in a motion to motivate the sling 7 attached to the instrument's proximal end 53 through the vaginal wall 60, behind the pubic bone 61, through the tissues of the abdominal wall 62, traversing the perforations made in the vaginal wall and abdominal wall made previously. A second sling instrument is then inserted on a portion of the body sufficiently distanced and positioned exactly on the opposite side of the body from the first sling transfer instrument with exact deployment steps completed to cause sling 7 to form a U-shape around mid-urethral and bladder neck sphincteric continence sites. Once so positioned, the sling is displaced from the sling transfer instrument subsequent to said sling proximal and distal end passage through the abdominal wall. Post position sling tension may be further accommodated via a sling tension measurement component that is discussed and disclosed in association with Parent application Ser. No. 10/308,735.

With respect to obturator fossa deployment, the procedure as described in association with transvaginal deployment is utilized with distinctions limited to the utilization of a progressively curved sling transfer instrument, as discussed in association with FIG. 6, and an exiting of sling transfer instrument tip 53 at a point allowing the tip 53 to exit through the obturator canal near the labia majora of the vagina instead of the suprapubic position.

With respect to the suprapubic method for treating urinary stress incontinence, a sling defining in part a tissue remodeling portion and a mesh section contoured to the anatomical configuration of the mid-urethra, proximal urethra and base of the bladder is provided. Said sling consistent with discussion and disclosure previously described in association with FIGS. 1 and 2. A sling transfer instrument having a distal end and a proximal end with a progressively curved portion positioned between said distal and proximal ends with an insertion handle is located at the instrument's proximal end. The sling transfer's insertion handle is positioned with a human hand and utilizing the handle, guides a curved tip at the instrument's distal end through the abdominal wall, through the retro pubic space allowing the tip of the instrument to maintain contact with the posterior surface of the pubic bone as it traverses the retro pubic space and continues into the vagina. A second sling instrument is next provided and similarly traverses through the abdominal wall, through the retro pubic space allowing the tip of the instrument to maintain contact with the posterior surface of the pubic bone as it traverses the retro pubic space as it continues into the vagina. The second instrument so deployed is positioned and deployed in a manner to allow attaching of the sling described in the parent application (Ser. No. 10/308,735) to be attached to the distal ends of the sling instruments so deployed. Cystoscopy is performed subsequent to the tip of both instruments being positioned in the vagina. Having attached the sling to the distal ends of both instruments, both instruments are withdrawn or otherwise positioned in such a manner to allow the distal ends of the sling transfer instruments to cause the attached sling to form a U-shape around the mid-urethral and bladder neck sphincteric continence sites. Once so positioned, the sling is displaced from both sling transfer instruments and sling tension adjustment may be facilitated by a sling tension measurement component as deemed necessary.

Figure 7:
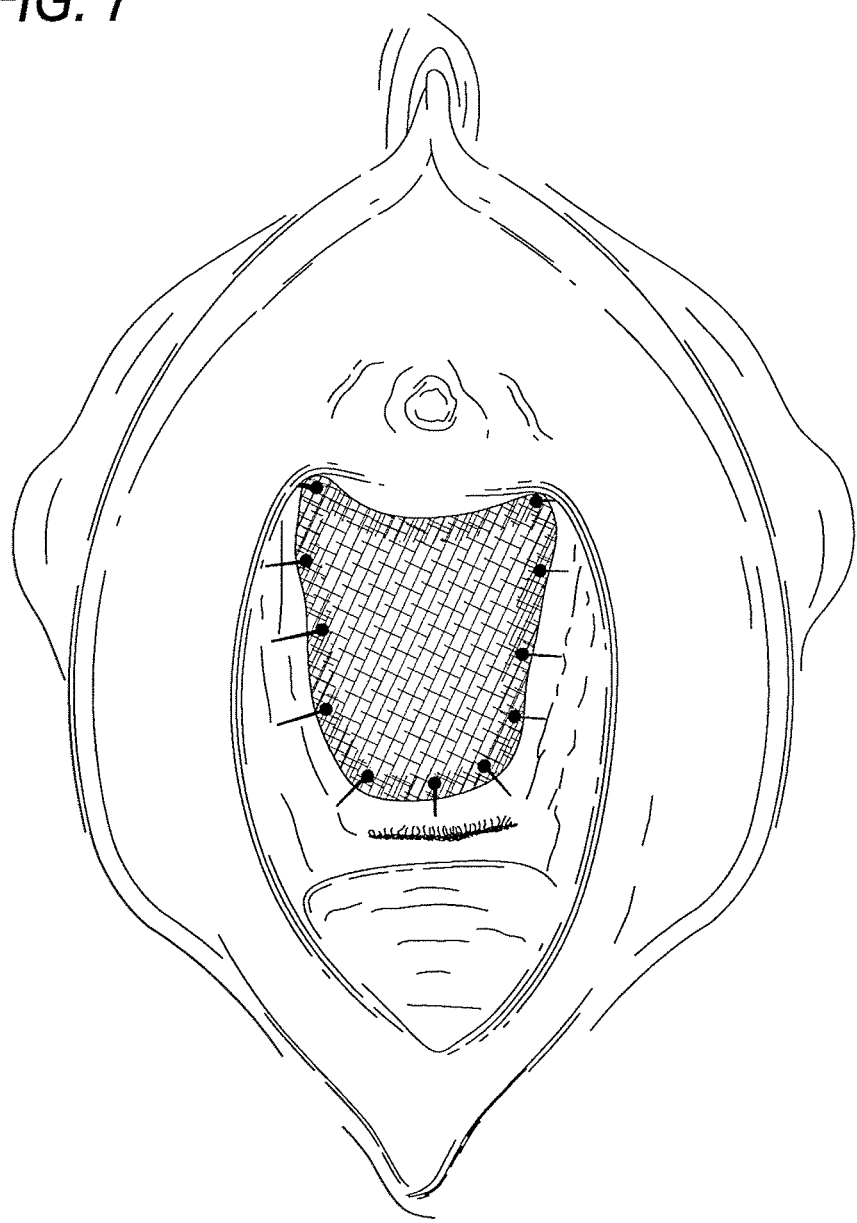
FIGS. 7 and 8 illustrate alternative embodiments of the tubular sling of the instant invention as deployed in extended continence support applications.
Figure 8:
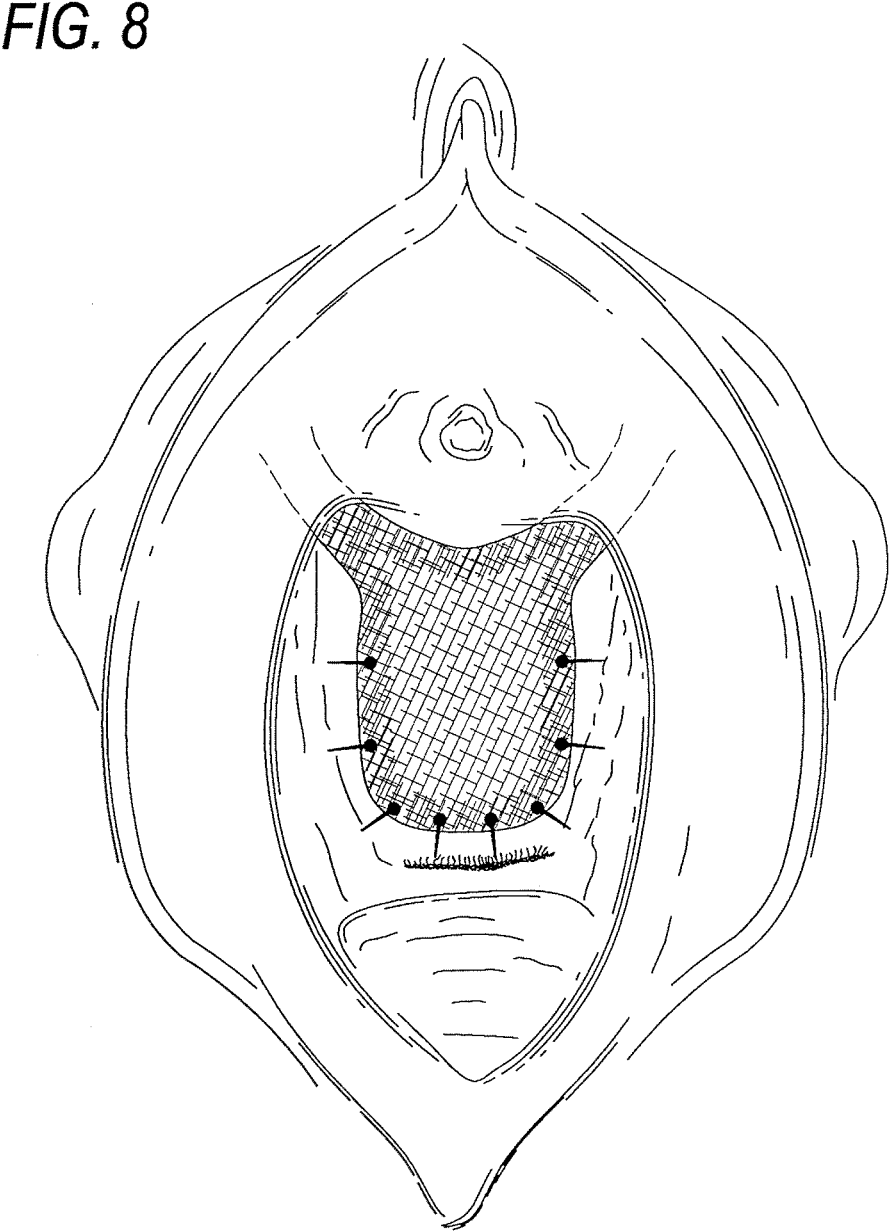

FIGS. 7 and 8 illustrate alternative embodiments of the tubular sling of the instant invention as deployed in extended continence support applications.

Figure 9:
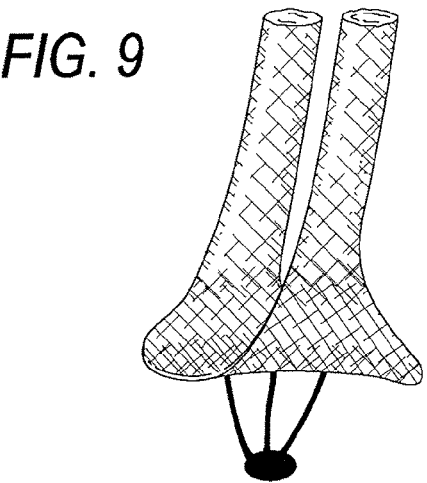
FIG. 9 is an illustration of the sling tension tab of the instant invention for decreasing tension providing further detail to allow for proper sling tension subsequent to deployment and positioning.

FIG. 9 is an illustration of the sling tension tab of the instant invention providing further detail to allow for proper sling tension subsequent to deployment and positioning.

Figure 10:
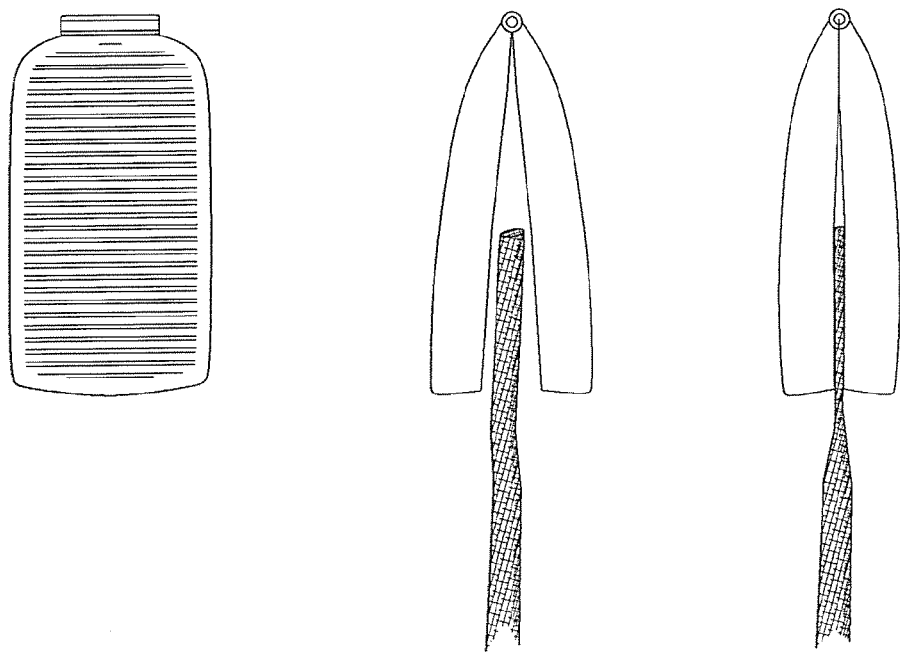
FIG. 10 is an illustration of the sling tension adjustment handle of the instant invention for increasing tension providing further detail to allow for proper sling tension subsequent to deployment and positioning.

FIG. 10 is an illustration of the sling tension adjustment handle of the instant invention for increasing tension providing further detail to allow for proper sling tension subsequent to deployment and positioning.

The claims and specifications describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While this invention has been described to illustrative embodiments, this description is not to be construed in a limiting sense. Various modifications and combinations of the illustrative embodiments as well as other embodiments will be apparent to those skilled in the art upon referencing this disclosure. It is therefore intended that this disclosure encompass any such modifications or embodiments.

It will of course be understood that various changes may be made in form, details, arrangement and proportions of the apparatus without departing from the scope of the invention, which generally stated consists of an apparatus capable of carrying out the objects above set forth, in the parts and combination of parts as disclosed and defined in the appended claims.

What is claimed is:

1. A surgical instrument for treating female urinary stress incontinence comprising:

a) a sling contoured to the anatomical configuration of the mid-urethra, proximal urethra, bladder neck and base of the bladder for implanting into the abdomen of a female providing support to mid-urethral and bladder neck sphincteric continence sites as well as support for the base of the bladder to restore the normal anatomical relationship of the urethra to the bladder, said sling defining in part a mesh section fixedly attached to and surrounding a tissue remodeling portion; and b) a sling transfer instrument having a distal end and a proximal end, said instrument defining in part a progressively curved shaft portion of a shaft positioned between distal and proximal ends of the shaft with a first detachable handle located at its proximal end, a second attachable handle positioned with reference to said shaft's distal end, and a means for attaching said sling to the proximal end of said shaft.

2. The surgical instrument of claim 1, wherein said first handle of said sling transfer instrument further comprises a digit control accommodation, said digit accommodation dimensioned approximately 2.5 to 4.5 cm length and 1.0 to 4.0 cm in width and approximately 1.5 cm in depth.

3. The surgical instrument of claim 1, wherein said progressively curved shaft portion of said transfer instrument has a diameter from about 3.5 mm to about 4.0 mm and a progressive curve with a maximum radius of approximately 5.1 cm.

4. The surgical instrument of claim 1, wherein a tip proximal end of said shaft portion of said transfer instrument is oriented in a direction opposite that of said shaft's curved portion, said proximal end of said shaft being 1.0 cm in length and approximately 4.0 mm in width at an end opposite that end attached to said curved shaft portion.

5. The surgical instrument of claim 1, wherein said progressively curved shaft portion of said transfer instrument has a diameter from about 3 mm to about 4.5 mm and a progressive curve with a maximum radius of approximately 4 cm.

6. The surgical instrument of claim 1, wherein the progressively curved shaft portion of said transfer instrument is further comprised of a luminous coating.

7. A surgical instrument for treating female urinary stress incontinence comprising:

a) a sling contoured to the anatomical configuration of the mid-urethra, proximal urethra, bladder neck and base of the bladder for implanting into the abdomen of a female providing support to mid-urethral and bladder neck sphincteric continence sites as well as support for the base of the bladder to restore the normal anatomical relationship of the urethra to the bladder, said sling defining in part a mesh section fixedly attached to and surrounding a tissue remodeling portion; and b) a sling transfer instrument having a distal end and a proximal end, said instrument defining in part a progressively curved shaft portion of a shaft positioned between distal and proximal ends of the shaft with a first detachable handle located at its proximal end, a second attachable handle positioned with reference to said shaft's distal end, and a means for attaching said sling to the proximal end of said shaft, wherein said mesh section of said sling is comprised of non-absorbable polymers, and filaments of said mesh have a diameter from about .002 inch to about .08 inch.

8. A surgical instrument for treating female urinary stress incontinence comprising:

a) a sling contoured to the anatomical configuration of the mid-urethra, proximal urethra, bladder neck and base of the bladder for implanting into the abdomen of a female providing support to mid-urethral and bladder neck sphincteric continence sites as well as support for the base of the bladder to restore the normal anatomical relationship of the urethra to the bladder, said sling defining in part a mesh section fixedly attached to and surrounding a tissue remodeling portion; and b) a sling transfer instrument having a distal end and a proximal end, said instrument defining in part a progressively curved shaft portion of a shaft positioned between distal and proximal ends of the shaft with a first detachable handle located at its proximal end, a second attachable handle positioned with reference to said shaft's distal end, and a means for attaching said sling to the proximal end of said shaft, wherein said mesh section of said sling is comprised of absorbable polymers and filaments of said mesh have a diameter from about .012 inch to about 0.1 inch.

9. A surgical instrument for treating female urinary stress incontinence comprising:

a) a sling contoured to the anatomical configuration of the mid-urethra, proximal urethra, bladder neck and base of the bladder for implanting into the abdomen of a female providing support to mid-urethral and bladder neck sphincteric continence sites as well as support for the base of the bladder to restore the normal anatomical relationship of the urethra to the bladder, said sling defining in part a mesh section fixedly attached to and surrounding a tissue remodeling portion; and b) a sling transfer instrument having a distal end and a proximal end, said instrument defining in part a progressively curved shaft portion of a shaft positioned between distal and proximal ends of the shaft with a first detachable handle located at its proximal end, a second attachable handle positioned with reference to said shaft's distal end, and a means for attaching said sling to the proximal end of said shaft, wherein said mesh section of said sling is approximately 4.0 cm in length, approximately 2.5 cm at its widest and generally center most position and approximately 1.0 cm wide at each of its opposite ends.

10. A transvaginal deployment method for treating female urinary stress incontinence comprising:

a) providing a sling defining in part a tissue remodeling portion and a mesh section and contoured to the anatomical configuration of the mid-urethra, proximal urethra and base of the bladder;

b) providing a sling transfer instrument having a distal end and a proximal end with a progressively curved shaft portion positioned between said distal and proximal ends with a detachable insertion handle located at the instrument's proximal end;

c) positioning the sling transfer instrument's detachable insertion handle within the human hand and using said handle to guide a curved tip at the instrument's distal end through the vaginal wall, behind the pubic bone, through the abdominal wall and exiting the abdominal wall below the pubic hair line;

d) disengaging the detachable insertion handle located at the instrument's proximal end from the progressively curved portion of sling transfer instrument;

e) attaching a sling transfer handle to the curved tip;

f) attaching the sling of step (a) to the sling transfer instrument's proximal end;

g) positioning the sling transfer instrument's sling transfer handle within the human hand and using said handle to retrieve or otherwise pull the sling attached to the instrument's proximal end through the vaginal wall, behind the pubic bone, through the tissues of the abdomen traversing perforations made in the vaginal wall and abdominal wall previously in step (c);

h) providing a second sling transfer instrument and repeating steps (c) through (g) on a side of the body to cause the sling to be positioned to form a U-shape around mid-urethral and bladder neck sphincteric continence sites;

i) displacing said sling from the sling transfer instrument subsequent to said sling's passage through the abdominal wall.

11. The method of claim 10 further comprising the adjusting of sling tension via a spring loaded tension measurement component.

12. A mesh sling comprising:
a central segment, wherein said central segment comprises a center most position, wherein biological tissue remodeling material is substantially surrounded and sandwiched between biodegradable mesh sections of said central segment; and
a first and a second distal segment connected to said central segment, wherein said first and second distal segments comprise biodegradable mesh polymer, wherein said first and second distal segments provide support around a urethra and a bladder neck.

13. The mesh sling as recited in claim 12, wherein said first and second distal segments possess a filament size of approximately 0.006 of an inch.

14. The mesh sling as recited in claim 12, wherein said central segment comprises a non-absorbable material.

15. The mesh sling as recited in claim 12, wherein said first and second distal segments attach in a graduating manner to said center most position, wherein said center most position is contoured to support anatomical variations in both mid-urethral and bladder neck continence sites.

16. The mesh sling as recited in claim 12, wherein said central segment comprises a fusiform shape.

17. A mesh sling comprising:
a central segment, wherein said central segment comprises a center most position, wherein biological tissue remodeling material is substantially surrounded and sandwiched between biodegradable mesh sections of said central segment;
a first and a second distal segment connected to said central segment, wherein said first and second distal segments comprise biodegradable mesh polymer, wherein said first and second distal segments provide support around a urethra and a bladder neck; and
supporting ribs throughout said first and second distal segments to secure said sling to surrounding tissues and to allow for sling tension adjustment.

18. The mesh sling as recited in claim 17, wherein said ribs pass transversely through said sling to secure said sling in position.

19. The mesh sling as recited in claim 17, wherein said first and second distal segments are approximately 1 centimeter in width.

20. A surgical instrument for treating female urinary stress incontinence comprising:
a tubular mesh sling comprising a central segment and a first and a second distal segment, wherein said central segment comprises a center most position, wherein biological tissue remodeling material is substantially surrounded and sandwiched between biodegradable mesh sections of said central segment, wherein said first and second distal segments comprise biodegradable mesh polymer, wherein said first and second distal segments provide support around a urethra and a bladder neck; and
a sling transfer instrument having a distal end and a proximal end, wherein said sling transfer instrument defining in part a progressively curved shaft portion of a shaft positioned between said distal and proximal ends of the shaft with a first detachable handle located at said proximal end, a second attachable handle positioned with reference to said distal end, and a means for attaching said tubular mesh sling to said proximal end of said shaft.

21. The surgical instrument as recited in claim 20, wherein said sling transfer instrument comprises a luminous coating.

* * * * *